United States Patent
Hirai et al.

(10) Patent No.: US 6,884,593 B1
(45) Date of Patent: Apr. 26, 2005

(54) METHOD OF IDENTIFYING PROPERTIES OF SUBSTANCE WITH RESPECT TO HUMAN PROSTAGLANDIN D2 RECEPTORS

(75) Inventors: Hiroyuki Hirai, Saitama (JP); Kazuyuki Ogawa, Saitama (JP); Kinya Nagata, Saitama (JP); Syoichi Takano, Saitama (JP)

(73) Assignee: BML, Inc., Tokyo (JP)

( * ) Notice: Subject to any disclaimer, the term of this patent is extended or adjusted under 35 U.S.C. 154(b) by 6 days.

(21) Appl. No.: 10/069,148

(22) PCT Filed: Aug. 22, 2000

(86) PCT No.: PCT/JP00/05615

§ 371 (c)(1),
(2), (4) Date: Jun. 24, 2002

(87) PCT Pub. No.: WO01/14882

PCT Pub. Date: Mar. 1, 2001

(30) Foreign Application Priority Data

Aug. 23, 1999 (JP) .............................................. 11/236207
May 24, 2000 (JP) ....................................... 2000/153172

(51) Int. Cl.⁷ ....................... G01N 33/53; G01N 33/567
(52) U.S. Cl. ........................... 435/7.1; 435/7.2; 435/7.8
(58) Field of Search ........................... 435/7.8, 7.1, 7.2; 530/350

(56) References Cited

U.S. PATENT DOCUMENTS

2002/0022218 A1    2/2002   Li et al.

FOREIGN PATENT DOCUMENTS

EP           1 170 594 A2      1/2002

OTHER PUBLICATIONS

Boie Yves et al: "Molecular cloning and characterization of the human prostanoid DP receptor," Journal of Biologic Chemistry, vol. 270, No. 32, 1992, pp. 18910–18916, XP002230274 ISSN: 0021–9258.

*Primary Examiner*—Robert Landsman
(74) *Attorney, Agent, or Firm*—Sughrue Mion, PLLC

(57) ABSTRACT

An object of the present invention is to provide a method of identifying a substance which acts on a newly found second human prostaglandin $D_2$ receptor subtype that differs from the DP receptor, and is useful for treating or preventing various diseases. In order to attain the object, the present invention provides a method of identifying properties of a test substance with respect to a human prostaglandin D receptor, by establishing correlation between the effect of a test substance on human CRTH2 with the effect of the test substance on the human prostaglandin D receptor.

11 Claims, 4 Drawing Sheets

* At the point in time indicated by the black arrow in each Fig., PGD$_2$ (final concentration: 25 nM) was added to the reaction mixture.

SEQUENCE LISTING

<160> NUMBER OF SEQ ID NOS: 2

<210> SEQ ID NO 1
<211> LENGTH: 34
<212> TYPE: DNA
<213> ORGANISM: Artificial Sequence
<220> FEATURE:
<223> OTHER INFORMATION: Forward PCR Primer

<400> SEQUENCE: 1
cttccgaagc tttcactcca gccctctgct cccg          34

<210> SEQ ID NO 2
<211> LENGTH: 39
<212> TYPE: DNA
<213> ORGANISM: Artificial Sequence
<220> FEATURE:
<223> OTHER INFORMATION: Reverse PCR Primer

<400> SEQUENCE: 2 gttctttct ataaaatgtg acatattcct cagcttacc          39

METHOD OF IDENTIFYING PROPERTIES OF SUBSTANCE WITH RESPECT TO HUMAN PROSTAGLANDIN D2 RECEPTORS

The present application is a national stage application under 35 U.S.C. §371 of PCT/JP00/05615, filed Aug. 22, 2000.

TECHNICAL FIELD

The present invention relates to a method of identifying a substance having specific properties.

BACKGROUND ART

Prostanoids, including prostaglandin, thromboxane, and leukotriene, belong to a family of oxidation metabolites from arachidonic acid, and play an important role in maintaining local homeostasis in the living body. Prostaglandin D2 ($PGD_2$), a member of the prostanoid family, is known to be synthesized in various organs including, in mammals, the brain, heart, spleen, lungs, kidneys, bone marrow, stomach, intestine, skin, uterus, and eyeballs, and is known to exhibit various physiological activities (Ujihara, M. et al., Arch. Biochem. Biophys., 260: 521–531, 1988; Ito, S. et al., Prostaglandins, Leukotrienes and Essential Fatty Acids, 37: 219–234, 1989; and references cited therein). In the central nervous system, $PGD_2$ is considered to participate in, for example, sleep introduction, regulation of body temperature, olfaction, hormone release, inflammation, and analgesia (Negishi, M. et al., Prog. Lipid Res., 32: 417–434, 1993, and the literature cited therein). Furthermore, $PGD_2$ is known to suppress agglutination of platelets, as well as to cause relaxation of smooth muscle in organs such as the blood vessels, stomach, intestine, and uterus (Giles, H. et al., Prostaglandins, 35: 277–300, 1988, and the literature cited therein). $PGD_2$ is a typical prostanoid released from a mast cell which plays an important role in immunological reactions. Moreover, $PGD_2$ is known to participate in formation of pathological conditions caused by allergy, such as allergic rhinitis and bronchial asthma, through actions such as contraction of bronchial smooth muscle, migration of eosinophiles to an inflammation site, and promotion of release of inflammatory mediators from mast cells, eosinophiles, and basophiles (Negishi, M. et al., Prog. Lipid Res., 32: 417–432, 1993, and the literature cited therein). In addition, when administered locally, $PGD_2$ has been demonstrated to have an effect to reduce intraocular pressure (Woodward, D. F. et al., Eur. J. Pharmacol., 230: 327–333, 1993).

On the basis of these findings, a substance exhibiting an action on a $PGD_2$ receptor; for example, a $PGD_2$-receptor-selective modulator (including an agonist and an antagonist), is considered to be a promising therapeutic drug for various diseases in which $PGD_2$ participates. For example, physiological actions of $PGD_2$ suggest that such a substance could be used as a wide range of drugs such as sedatives/sleeping drugs, analgesics, drugs for regulating blood pressure, platelet agglutination inhibitors, drugs for circulatory organs, drugs for suppressing motions of the stomach and intestine, anti-gastric ulcer drugs, therapeutic drugs for allergy, anti-inflammatory drugs, and prophylactic or therapeutic drugs for glaucoma.

Presently, $PGD_2$ has been elucidated to exert its effects via a specific receptor (Coleman, R. et al., Pharmacol. Rev., 46: 205–229, 1994). However, it is known that the reaction between $PGD_2$ and its receptor has species specificity, and thus, limitation is imposed on drug screening or evaluation or efficacy of a drug using animal tissue or an animal model (Narumiya, S. et al., Br. J. Pharmacol., 85: 367–375, 1985).

Also, a number of pharmacological analyses suggest that, with respect to human and animals, at least two subtypes of $PGD_2$ receptor mediate various pharmacological actions of $PGD_2$ (Woodward, D. F. et al., Eur. J. Pharmacol., 230: 327–333, 1993; Fernandes, B. et al., Eur. J. Pharmacol., 283: 73–81, 1995). For example, in human uterus smooth muscle, existence of two subtypes of $PGD_2$ receptors; one mediating contraction caused by $PGD_2$ and the other, conversely, mediating relaxation, has been suggested (Fernandes, B. et al., Eur. J. Pharmacol., 283: 73–81, 1995). Therefore, development of a drug which exclusively modulates, among the various actions of $PGD_2$, a specific action of $PGD_2$ related to prevention or improvement of pathological conditions requires understanding of the distribution of $PGD_2$ receptor subtypes in human organs and isolation of the cDNA which codes the receptor subtypes.

Recently, after enormous research efforts, a gene which is considered to be a $PGD_2$ subtype (hereinafter may be referred to as a DP receptor) has been cloned (Boie, Y. et al., J. Biol. Chem., 270: 18910–18916, 1995; Japanese Kokyo (PCT) Publication No. 10-507930).

Currently, studies are being conducted in order to identify, among a variety of physiological activities exhibited by $PGD_2$, the specific physiological activity or activities in which the DP receptor participates. As a result of such studies, one report describes that analysis on the DP receptor, through expression in the rat brain, has revealed that distribution of the DP receptor does not coincide with the sleep induction sensitive region of $PGD_2$ (Gerashchenko, D. et al., J. Neurochem., 71: 937–945, 1998). That is, this report suggests the presence of a $PGD_2$ receptor which is different from the DP receptor, and thus, verification of the presence of such a new receptor and identification of the functions thereof are of keen interest.

The subject matter to be handled by the present invention is to find a second human $PGD_2$ receptor subtype other than the DP receptor, and to provide a method of identifying a substance which acts on the second human $PGD_2$ receptor subtype and which is useful in the treatment and prevention of a variety of diseases; for example, a substance which acts as a selective modulator (including an agonist and an antagonist).

DISCLOSURE OF THE INVENTION

Quite unexpectedly, the present inventors have found, during the course of their studies on G-protein-coupling-receptor-like protein human CRTH2 (hereinafter may be referred to simply as human CRTH2) [Nagata, K. et al., J. Immunol., 162: 1278–1286, 1999, and Japanese Sai-Kohyo (PCT) Patent Publication WO 97/46677 (this patent publication describes human CRTH2 as "B19")] obtained by genetic cloning by use of human lymphocytes is an attempt to search for its physiological ligands, that human CRTH2 selectively reacts with $PGD_2$. Further, as a result of comparison between the human CRTH2 and the DP receptor, they have found that the human CRTH2 and the DP receptor react differently with the $PGD_2$-like substance. Moreover, they have confirmed that a certain compound (e.g., human CRTH2 antibody) can exert selective antagonist activity against human CRTH2, without affecting the DP receptor.

Thus, human CRTH2, which initially had been considered to be irrelevant to $PGD_2$, has surprisingly been concluded to be precisely the aforementioned second human $PGD_2$ receptor subtype of interest.

The present invention is therefore drawn to a method of identifying a substance, which is capable of determining a useful substance having connection with human $PGD_2$ and which employs a specific property of the human CRTH2; i.e., the capability of acting as a $PGD_2$ receptor subtype.

Thus, in the present patent application, the present inventors provide a method of identifying a test substance (hereinafter may be referred to as the present identification method); specifically, a method of identifying the properties of the test substance with respect to a human prostaglandin D receptor, by determining the correlation between the effect of the test substance on human prostaglandin D receptor (for example, selective modulator effect on the receptor) and the effect of the same test substance on human CRTH2.

In the present invention, the term "modulator effect" means any effect that affects the function of the prostaglandin receptor of interest, such as inhibitory effect against the receptor (typically, effect exhibited by an antagonist) or promotion effect (typically, effect exhibited by an agonist), but is not limited thereto.

BEST MODE FOR CARRYING OUT THE INVENTION

Figure 1:
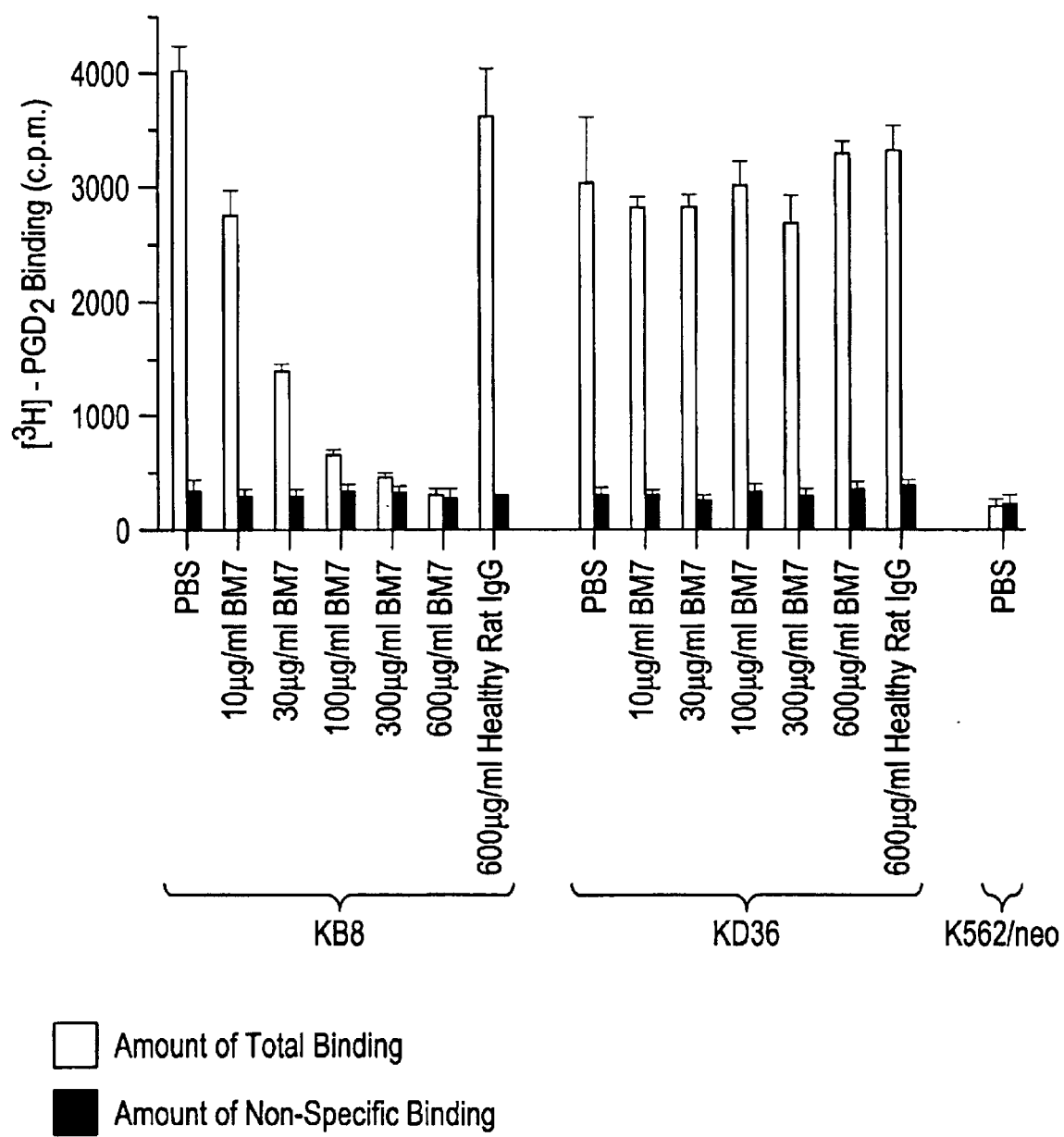
FIG. 1 shows the results of an assay, performed in accordance with the method described in Example 3, investigating the [$^3$H]$PGD_2$ binding ability of cells expressing human CRTH2 (KB8) or DP receptor (KD36)

Embodiments of the present invention will next be described.

A. Human CRTH2

The present identification method is based on the finding that human CRTH2, which is a known human protein, functions as a second human $PGD_2$ receptor subtype that differs from the DP receptor.

Human CRTH2 refers to a human-derived protein registered as "accession number AB008535" in databases DDBJ, EMBL, and GenBank, and the nucleotide sequence of cDNA of human CRTH2 and the amino acid sequence encoded by the sequence are known. The nucleotide sequence and the amino acid sequence are freely available from the aforementioned databases or publications [Nagata, K. et al., J. Immunol., 162: 1278–1286, 1999 and Japanese Sai-Kohyo (PCT) Patent Publication WO 97/46677 (this patent publication describes human CRTH2 gene as "B19 gene")].

These known data enable preparation of a cloned human CRTH2 protein or a partial peptide thereof, cells expressing human CRTH2, or cell fractions containing human CRTH2, and the thus-prepared products can be used in the present identification method.

(1) Preparation of Human CRTH2 or a Partial Peptide Thereof

For example, a partial peptide or full-length peptide of human CRTH2 can be obtained through chemical synthesis by means of a known method. More typically, cDNA encoding any of a full-length peptide of human CRTH2, a modified peptide of human CRTH2 in which a portion of amino acids is substituted, deleted, or added, and a partial peptide of human CRTH2 (hereinafter these peptides may be collectively referred to as "human CRTH2-related protein") is prepared; the resultant cDNA is integrated into an appropriate expression vector; an appropriate host cell is transformed by the expression vector; and a recombinant human CRTH2-related protein can be produced from the resultant transformant.

Cloning and recombination of human CRTH2 cDNA can be carried out by means of a standard technique known in the art. The standard technique is described in detail in, for example, Maniatis, T. et al., Molecular Cloning: A Laboratory Manual (Cold Spring Harbor Laboratory, Cold Spring Harbor, N.Y., 1989). Gene modification can be carried out by means of a known method; for example, site-specific mutagenesis (Mark, D. F., et al., Proc. Natl. Acad. Sci. U.S.A, 81, 5662 (1984)).

In order to express recombinant human CRTH2 in an appropriate host cell, generally, on the basis of known nucleotide sequence data of human CRTH2 cDNA, DNA encoding a human CRTH2-related protein (typically, human CRTH2 cDNA) is cloned in an expression vector. For example, human CRTH2 cDNA can be isolated through known reverse transcription polymerase chain reaction (RT-PCR) by use, as a template, of poly(A) RNA extracted from tissue in which enhancement of expression of a human CRTH2 gene is reported ("PCR Protocols, A Guide to Methods and Applications" edited by Innis, M. A., et al., Academic Press, San Diego, 1990). Examples of human tissue in which expression of a human CRTH2 gene is enhanced include Th2-type T lymphocytes (Nagata, K. et al., J. Immunol., 162: 1278–1286, 1999), eosinophiles, and basophiles.

There may be employed a traditional technique for obtaining full-length human CRTH2 cDNA from, for example, a cDNA library derived from the aforementioned tissue in which human CRTH2 is highly expressed. This can be achieved by use, as a probe, of a fraction of human CRTH2 cDNA amplified through PCR as described above, or chemically synthesized DNA or RNA complementary to the nucleotide sequence of human CRTH2. Such a traditional technique is described in detail in, for example, Maniatis, T. et al., Molecular Cloning: A Laboratory Manual (Cold Spring Harbor Laboratory, Cold Spring Harbor, New York, 1989).

An expression vector into which DNA encoding a human CRTH2-related protein, such as human CRTH2 cDNA, is to be integrated preferably has a promoter and an enhancer at the upstream site of a gene to be expressed, and a transcription termination sequence at the downstream site of the gene. Expression of a human CRTH2 gene may be carried out in a direct expression system or in a fusion protein expression system utilizing, for example, a β-galactosidase gene, a glutathione-S-transferase gene, or a thioredoxin gene.

Examples of gene expression vectors employing *Escherichia coli* as a host include pQE, pGEX, pT7-7, pMAL, pTrxFus, pET, and pNT26CII. Examples of gene expression vectors employing *Bacillus subtilis* as a host include pPL608, pNC3, pSM23, and pKH80. Examples of gene expression vectors employing yeast as a host include pGT5, pDB248X, pART1, pREP1, YEp13, YRp7, and YCp50. Examples of gene expression vectors employing a mammal cell or insect cell as a host include p91023, pCDM8, pcDL-SRα296, pBCMGSNeo, pSV2dhfr, pSVdhfr, pAc373, pAcYM1, pRc/CMV, pREP4, and pcDNAI.

These gene expression vectors may be chosen in accordance with purposes of expression of a human CRTH2-related protein. For example, when expression of large amounts of human CRTH2-related proteins is desired, a gene expression vector which can employ *Escherichia coli, Bacillus subtilis,* or yeast as a host is preferably selected. When expression of small amounts of human CRTH2-related proteins reliably exhibiting activity is desired, a gene expression vector which can employ a mammal cell or insect cell as a host is preferably selected. As described above, an existing gene expression vector may be selected, but, in accordance with purposes, a new gene expression vector may be produced appropriately, and used.

Introduction, into a host cell, of an expression vector containing a gene encoding a human CRTH2-related protein, and transformation of the host cell by the vector can be carried out by means of a routine method. For example, when the host is *Escherichia coli* or *Bacillus subtilis,* a calcium chloride method or electroporation can be employed. When the host is a mammal cell or an insect cell, calcium phosphate transfection, electroporation, or a liposome method can be employed.

When the thus-obtained transformant is cultured by means of a customary method, a desired human CRTH2-related protein is accumulated. A culture medium used in the culture may be appropriately chosen in accordance with the properties of the host cell. For example, when the host is *Escherichia coli,* an LB medium, a TB medium, etc. can be used. When the host is a mammal cell, an RPMI1640 medium, etc. can be used.

The recombinant human CRTH2-related protein obtained through the aforementioned procedure is isolated and purified, and can be used as a pure human CRTH2 protein. The human CRTH2-related protein is purified by means of a known technique. Examples of the purification technique include cell solubilization, treatment with a protein precipitant, ultrafiltration, gel filtration, high performance liquid chromatography, centrifugation, electrophoresis, affinity chromatography making use of a specific antibody or a specific ligand, and dialysis. These techniques may be used singly or in combination of two or more. A typical purification method for prostanoid receptor is described in, for example, Ushikubi, F. et al., J. Biol. Chem., 264: 16496–16501, 1989, and purification of the human CRTH2-related protein may be carried out by means of this method.

(2) Cell in which Humans CRTH2 is Expressed, or Cell Fraction, etc. Containing Human CRTH2

Instead of the aforementioned recombinant human CRTH2-related protein, human tissue, a human cell strain, etc. in which natural human CRTH2 is highly expressed may be used in the present identification method. Alternatively, a transformant which has been transformed by a gene encoding the aforementioned human CRTH2-related protein may be used. In such a human tissue, human cell strain, etc., preferably, only human CRTH2 is expressed, and the DP receptor and other prostanoid receptors are not expressed.

A human-CRTH2-expressing cell per se can be used in the present identification method. Also, cell fractions containing a human CRTH2 protein (for example, membrane components obtained through supersonic fragmentation treatment and ultracentrifugation) can be obtained from the cell and used.

As described in (1) and (2), a cloned human CRTH2-related protein, a cell in which human CRTH2 is expressed, or a cell fraction containing human CRTH2 (hereinafter these protein, cell, and cell fraction may be collectively referred to as "human CRTH2, etc.") can be prepared. The thus-prepared product can be used in the present identification method.

B. Description of the Present Identification Method

As described above, in the present identification method, the effect of a test substance on human CRTH2, etc. is correlated with the effect of the test substance on a human prostaglandin D receptor. Prior to this correlation, the effect of the test substance on human CRTH2, etc. must be specified.

Typical effects of the test substance on the human prostaglandin D receptor include selective modulator effect with respect to a human prostaglandin D receptor subtype.

The following descriptions will mainly deal with the selective modulator effect.

As described above, the present identification method is based on the finding that human CRTH2 functions as a second human $PGD_2$ receptor subtype that differs from the DP receptor, which is the "first human $PGD_2$ receptor subtype." Therefore, when a test substance is identified as a selective modulator for activation of human CRTH2, the test substance can be identified as a selective modulator with respect to the second human $PGD_2$ receptor. As described above, the selective modulator with respect to activation of human CRTH2 is identified by evaluating, for example, its selective binding ability with respect to human CRTH2 or its selective effect on the function of human CRTH2, by use of, for example, a cloned human CRTH2 protein or a partial peptide thereof, a cell expressing human CRTH2, or a cell fraction containing human CRTH2.

As described above, the present identification method can employ various molecular forms of human CRTH2. However, in order to evaluate the activity of a selective modulator with respect to human CRTH2, in general, several points must be considered. Firstly, the minimum domain of human CRTH2 required for substantial interaction between human CRTH2 and $PGD_2$ has not yet been elucidated. Therefore, at present, instead of using a partial peptide of human CRTH2, use of a full-length human CRTH2 protein may be desirable. A human CRTH2 protein derivative— which is formed through substitution or removal of a portion of amino acids of a human CRTH2 protein—may undergo change in ligand selectivity. Therefore, a protein having the same amino acid sequence as that of a naturally occurring human CRTH2 protein may be preferably used. Meanwhile, a sugar chain(s) is bonded to the extracellular site of human CRTH2 which exists as a human membrane protein, and the sugar chain may be necessary for effective interaction between human CRTH2 and $PGD_2$. Therefore, a host employed for expression of human CRTH2 may be preferably a host cell which enables addition of sugar chain to human CRTH2. In this case, the function of human CRTH2 may vary in accordance with the type of sugar chain. Therefore, until sufficient data in relation to the structure of the sugar chain are obtained, a mammal cell may be preferably used as a host cell. When large amounts of human CRTH2 modulators are subjected to screening, the aforementioned modified human CRTH2, partial peptide of human CRTH2, etc. may be advantageously used. Therefore, in accordance with purposes, molecular forms of human CRTH2 employed may be chosen.

When a selective modulator with respect to activation of human CRTH2, etc. is identified by means of the present identification method, no absolute limits are imposed on a test substance. Briefly, in the present identification method, a test substance may be a naturally occurring product (including a recombinant protein produced through biotechnological technique) or a chemically synthesized product. When the present identification method is carried out, if necessary, a known labeled or unlabeled ligand (for example, prostanoid such as $PGD_2$) may be used.

No particular limitation is imposed on the method for identifying the effect of a test substance on human CRTH2, etc., and the effect may be determined by means of any assay known in the art. For example, prostanoid receptor binding assay is described in, Boie, Y. et al., J. Biol. Chem., 270: 18910–18916, 1995.

Typical means for correlating the effect of a test substance on human CRTH2, etc. (for example, a selective modulator effect) with the effect of the test substance on a human prostaglandin D receptor include (1) means in which the binding ability of the test substance with respect to a human CRTH2-related protein is used as an index.

When the means (1) is carried out, the binding ability of a test substance with respect to purified human CRTH2 can be determined directly by use of, for example, an apparatus employing surface plasmon resonance as a measurement principle [e.g., Biacore 2000 (product of Amersham Pharmacia)] (see, e.g., a method described in Boris, J. et al., J. Biol. Chem., 272: 11384–11391, 1997). A labeled test substance can be used in the test for directly measuring the binding ability of the test substance with respect to human CRTH2. As described above, the binding ability of a test substance with respect to human CRTH2 can be measured on the basis of, as an index, inhibition or enhancement of the binding of human CRTH2 to a known labeled ligand (e.g., [$^3$H]-labeled $PGD_2$) (see, e.g., a method described in Boie, Y. et al., J. Biol. Chem., 270: 18910–18916, 1995).

If binding ability of a test substance with respect to a human CRTH2-related protein is acknowledged through the means (1), it is very likely that the test substance is a modulator which provides any effect, such as inhibition effect or enhancement effect, on a human prostaglandin D2 receptor.

The aforementioned typical means also include (2) means in which the action, as an agonist, of a test substance with respect to a human prostaglandin D receptor is used as an index.

The action, as an agonist, of a test substance with respect to a human prostaglandin D receptor can be determined by evaluating in situ activation of human CRTH2 by the test substance, or the effect of the test substance (i.e., inhibition or augmentation) on activation of human CRTH2 by $PGD_2$. In this case, activation of human CRTH2 can be measured on the basis of, as an index, an increase in the concentration of $Ca^{2+}$ in a host cell (see, e.g., a method described in Boie, Y. et al., J. Biol. Chem., 270: 18910–18916, 1995); enhancement of migration (see, e.g., a method described in Yokomizo, T. et al., Nature, 387: 620–624, 1997); or down modulation of human CRTH2 molecules at a cell surface (see, e.g., a method described in Luttrell, L. M. et al., Science, 283: 655–661, 1999). Examples of the mammal cell strain used as a host when activation of human CRTH2 is measured include K562, Jurkat, HEK293, and CHO.

In the case in which the means (2) is carried out, when in situ activity of a human CRTH2 receptor is enhanced by a test substance, the test substance is identified as an agonist which enhances activity of a human prostaglandin D2 receptor. In contrast, when the receptor activity is reduced by a test substance, the test substance is identified as an antagonist which reduces activity of the human prostaglandin D2 receptor.

Selective modulators with respect to human CRTH2 (i.e., a second human $PGD_2$ receptor) are useful for treating and preventing pathological conditions related to the second human $PGD_2$ receptor, among various pathological conditions related to $PGD_2$. Although pathological conditions related to the second human $PGD_2$ receptor have not yet been fully specified, the aforementioned modulators are expected to find use as drugs for various pathological conditions related to $PGD_2$, including sedatives/hypnotics, analgesics, blood pressure regulating drugs, platelet aggregation inhibitors, drugs for circulatory organs, drugs for suppressing motions of the stomach and the intestine, antigastric ulcer drugs, allergy therapeutic drugs, antiinflammatory drugs, and drugs for preventing and treating glaucoma.

As described above, the properties of a test substance with respect to prostaglandin D or a human prostaglandin D receptor are identified by correlating the effect of the substance on human CRTH2 (for example, a selective modulator effect) with the effect of the substance on the human prostaglandin D receptor. When the identification method is used for, for example, screening of drugs, it can greatly contribute to the relevant industry.

EXAMPLES

The present invention will next be described in more detail by way of Examples, which should not be construed as limiting the invention thereto.

Example 1

Preparation of a Cell in which Human CRTH2 is Expressed

Human CRTH2 gene expression plasmid pRc/B19 was prepared by means of a method described in detail in Nagata, K. et al., J. Immunol., 162: 1278–1286, 1999 and Japanese Sai-Kohyo (PCT) Patent Publication WO 97/46677. A transformant into which full-length human CRTH2 cDNA is integrated is deposited as B19 cDNA in National Institute of Bioscience and Human-Technology, Agency of Industrial Science and Technology (deposit number: FERM P-15616), and B19 cDNA can be used after approval is obtained from the depositor. When B19 cDNA is digested with restriction enzymes HindIII and XbaI, and is subcloned into the HindIII/XbaI site of plasmid pRc/CMV (product of Invitrogen), the same expression plasmid as the aforementioned pRc/B19 can be prepared. Through electroporation, the pRc/B19 and control plasmid pRc/CMV were genetically introduced into K562 cells, a human erythroblastic leukemia cell strain, and were subjected to selective culture for two to three weeks in the presence of 400 μg/ml of geneticin (product of SIGMA). Among the K562 cells into which the pRc/B19 had been genetically introduced, the survived cells were added to a 96-well microplate (0.3 cells per well), and then cultured for two to three weeks. The proliferated cell clones were subjected to fluorescence staining by use of an anti human CRTH2 antibody (Nagata, K. et al., J. Immunol., 162: 1278–1286, 1999), and clone KB8, in which human CRTH2 was highly expressed, was obtained. The K562 cells into which the control pRc/CMV had been genetically introduced were selected by use of geneticin, and then culture of the resultant cells was continued while polyclones were present (hereinafter the cells will be referred to as "K562/neo").

Example 2

Preparation of Comparative Cell in which DP Receptor is Expressed

Human DP receptor cDNA was cloned through RT-PCR on the basis of the nucleotide sequence of human DP receptor cDNA described in Boie, Y. et al., J. Biol. Chem., 270: 18910–18916, 1995 and Japanese Kohyo (PCT) Patent Publication No. 10-507930. Specifically, the cDNA was prepared by use, as an template, of poly(A)+RNA (product of Clonetech) of the human small intestine in which the human DP receptor is highly expressed, and by use of oligo (dT) primer (product of Pharmacia) and MMLV reverse transcriptase (product of Pharmacia). Subsequently, the coding region of the human DP receptor was amplified through PCR (35 heat cycles, each cycle consisting of heating at 94° C. for 1 minute, at 68° C. for 1 minute, and at 72° C. for 1 minute) by use of a forward primer (5'-CTTCCGAAGCTTTCACTCCAGCCCTCTGCTCCCG: SEQ No. 1) containing a restriction enzyme HindIII site, and a reverse primer (5'-GTTCTTTTCTATAAAATGTGACATATTC-CTCAGCTTACC: SEQ No. 2) containing an XbaI site. The resultant PCR product was digested with HindIII and XbaI, and subcloned into the HindIII/XbaI site of pRc/CMV. The thus-prepared human DP receptor expression plasmid was introduced into a K562 cell in a manner similar to that described in Example 1, and subjected to selection by use of geneticin and to cloning. The proliferated clones were subjected to the below-described [$^3$H]PGD$_2$ binding assay, to thereby obtain clone KD36 in which the DP receptor is highly expressed.

Example 3

[$^3$H]PGD$_2$ Binding Assay

Each of KB8 cells, KD36 cells, and K562/neo cells was resuspended in Hank's balanced salt solution (HBSS, product of Gibco BRL) so as to attain a concentration of 3×10$^7$ cells/ml. The resultant suspension (0.1 ml) was placed in a 0.5-ml microtube, and then cooled on ice. Subsequently, 1 nM of [$^3$H]PGD$_2$ (product of Amersham) which had been diluted with HBSS was added to the suspension, to thereby allow reaction to proceed on ice for one hour. The reacted cells were placed carefully onto RPMI1640 medium (1 ml) containing 1 M sucrose and 10% fetal bovine serum, the medium having been placed in an 1.5-ml microtube and cooled by ice, and subjected to centrifugation (10,000 revolutions, three minutes) by use of a micro-centrifuge. After the supernatant was aspirated from the tube such that the mixture (about 0.1 ml) remained in the tube, the mixture was further subjected to centrifugation (10,000 revolutions, one minute) such that the reaction mixture did not remain on the tube wall, and subsequently the supernatant was removed as carefully as possible so as to avoid removing the cells. The radiation activity of the cells bound to [$^3$H]PGD$_2$ was measured by use of a liquid scintillation counter. The radiation activity of the cells when measured, in a manner similar to that described above, in the presence of unlabeled PGD$_2$ (concentration: 200 times or more that of [$^3$H]PGD$_2$) was used as an index of non-specific binding. As a result, as shown in FIG. 1, the specific binding of [$^3$H]PGD$_2$ to K562/neo is not observed. In contrast, the specific binding of [$^3$H]PGD$_2$ to KB8 or KD36 is observed. In this measurement system, anti CRTH2 antibody BM7 (Nagata, K. et al., J. Immunol., 162: 1278–1286, 1999 and Nagata, K., et al., FEBS Lett., 459: 195–199, 1999) selectively inhibited the binding of [$^3$H]PGD$_2$ to KB8 in a concentration-dependent manner. The results show that this method can identify a selective modulator with respect to human CRTH2, which does not act on the DP receptor.

Example 4

Intracellular Calcium Assay

Figure 2:
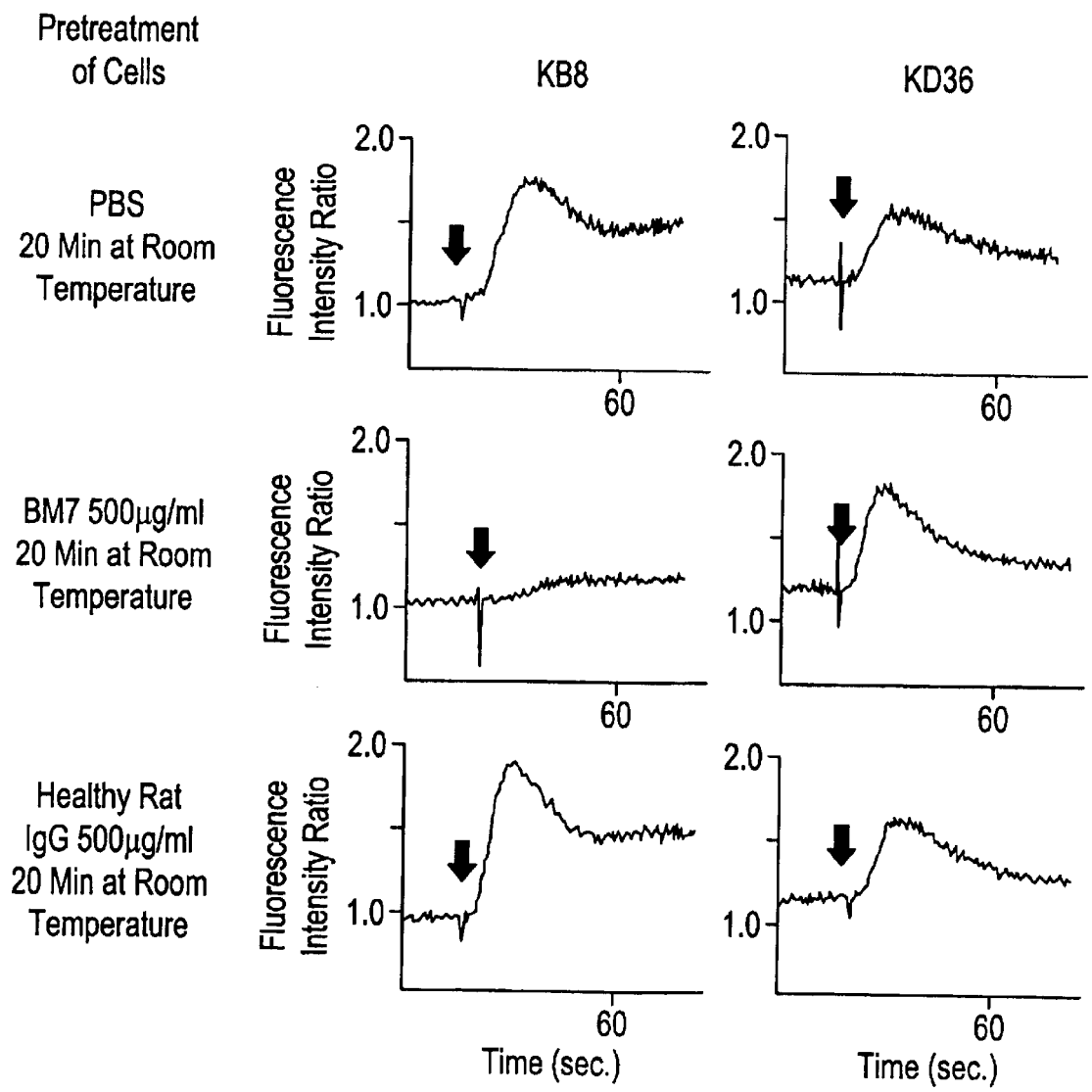
FIG. 2 shows the results of an intracellular calcium assay, performed in accordance with the method described in Example 4, investigating the reaction, with $PGD_2$, of cells expressing human CRTH2 (KB8) or DP receptor (KD36)

Each of KB8 cells, KD36 cells, and K562/neo cells was suspended in RPMI1640 medium containing 10% fetal bovine serum so as to attain a concentration of 5×10$^6$ cells/ml, and cultured at 37° C. for one hour in the presence of 5 µM of Fura-2AM (product of Dojindo). After completion of culturing, the cells were washed three times with HBSS through centrifugation, to thereby remove free Fura-2AM. Subsequently, the resultant cells were resuspended in HBSS containing 0.1% bovine serum albumin so as to attain a concentration of 10$^6$ cells/ml. The resultant suspension was placed in a quartz cell (volume: 0.4 ml), and the cell was set in spectrophotometer LS50B (product of PerkinElmer). After a sample was added to the suspension, the time-course change of the ratio of fluorescence intensities (510 nm) at excitation wavelengths of 340 nm and 380 nm was obtained through calculation by use of FL-Winlab software (product of PerkinElmer). In the case of K562/neo, the concentration of calcium in the cells did not vary significantly by treatment with PGD$_2$ (0.25–250 nM). In contrast, in the case of KB8 or KD36, the concentration of calcium in the cells increased considerably by treatment with PGD$_2$ (some nM). In this measurement system, anti-CRTH2 antibody BM7 exhibited selectively antagonistic activity with respect to human CRTH2 (FIG. 2). These results show that this method can identify a selective modulator with respect to human CRTH2, which does not act on the DP receptor.

Example 5

Binding Activity of Various Prostanoids with Respect to Human CRTH2

Figure 3:
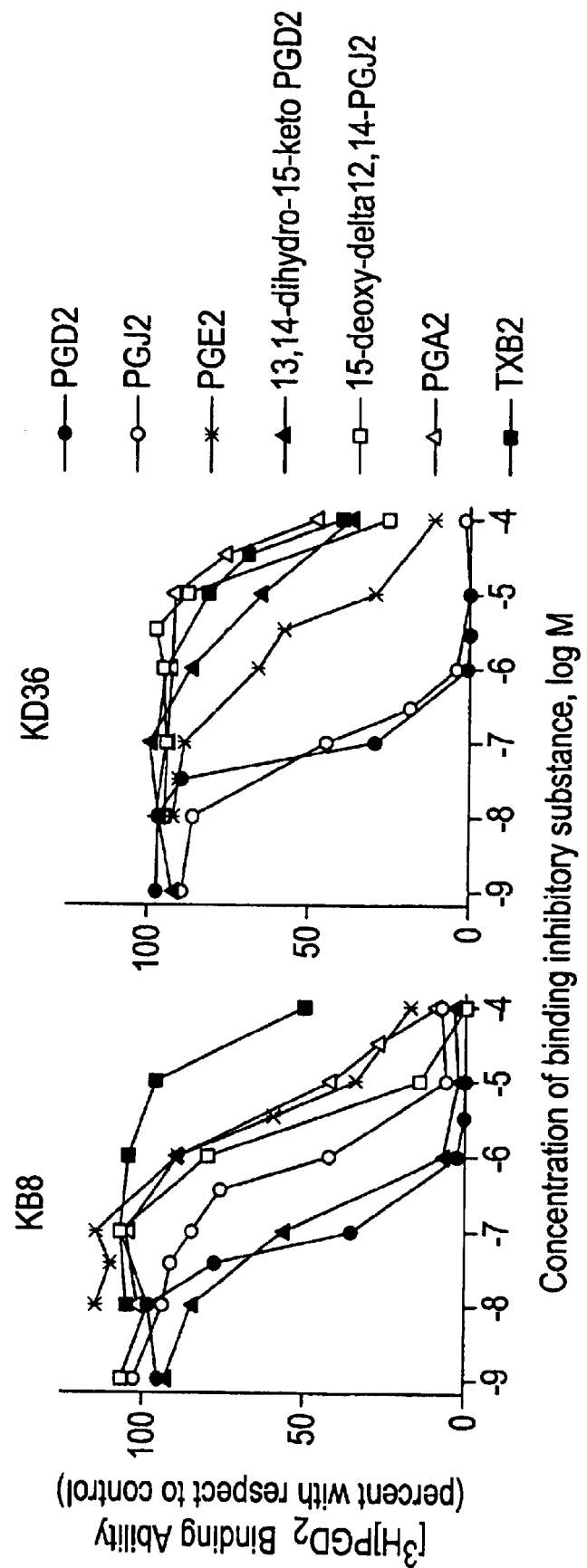
FIG. 3 shows the results of an assay, performed in accordance with the method described in Example 5, investigating the ligand selectivity of human CRTH2 and that of DP receptor.

[$^3$H]PGD$_2$ binding assay described in Example 3 was carried out in the presence of various unlabeled prostanoids (products of Cayman), and the binding affinity of human CRTH2 to various prostanoids was evaluated. As a result, the order of the degree of the binding affinity of prostanoids to human CRTH2 was determined as follows: PGD$_2$≧13,14-dihydro-15-keto PGD$_2$>>prostaglandin J$_2$ (PGJ$_2$)>15-deoxydelta 12,14-PGJ$_2$≧prostaglandin E$_2$ (PGE$_2$)= prostaglandin A$_2$ (PGA$_2$)>>thromboxane B$_2$ (TXB$_2$) (FIG. 3). For comparison, the order of the degree of the binding affinity of prostanoids to the DP receptor was determined as follows: PGD$_2$=PGJ$_2$>>PGE$_2$>13,14-dihydro-15-keto PGD$_2$>15-deoxydelta 12,14-PGJ$_2$≧TXB$_2$≧PGA$_2$. These results show that the degree of the binding affinity of human CRTH2 to PGD$_2$ is equal to that of the binding affinity of the DP receptor to PGD$_2$, and that a great difference exists between human CRTH2 and the DP receptor in the degree of binding affinity to other prostanoids, such as 13,14-dehydro-15-keto PGD$_2$.

Example 6

Down Modulation of Human CRTH2 Molecules by Selective Agonist

KB8 cells were suspended in RPMI1640 medium containing 10% fetal bovine serum so as to attain a concentration of 10$^6$ cells/ml, and cultured at 37° C. for one hour in the presence of a test sample. After completion of culturing, the cells were washed twice with HBSS through centrifugation, to thereby remove cell-free part of the sample. Subsequently, the resultant cells were resuspended in HBSS containing 0.5% bovine serum albumin and 0.05% NaN$_3$, and the resultant suspension was subjected to fluorescence staining by use of anti CRTH2 monoclonal antibody HM16 and phycoerythrin-labeled anti rat immunoglobulin antibody. The average fluorescence intensity of the stained cells was measured by use of a flow cytometer (product of Becton Dickinson), and the fluorescence intensity of the cells treated with the sample was compared with that of non-treated cells (control). The results are shown in FIG. 4.

Figure 4:
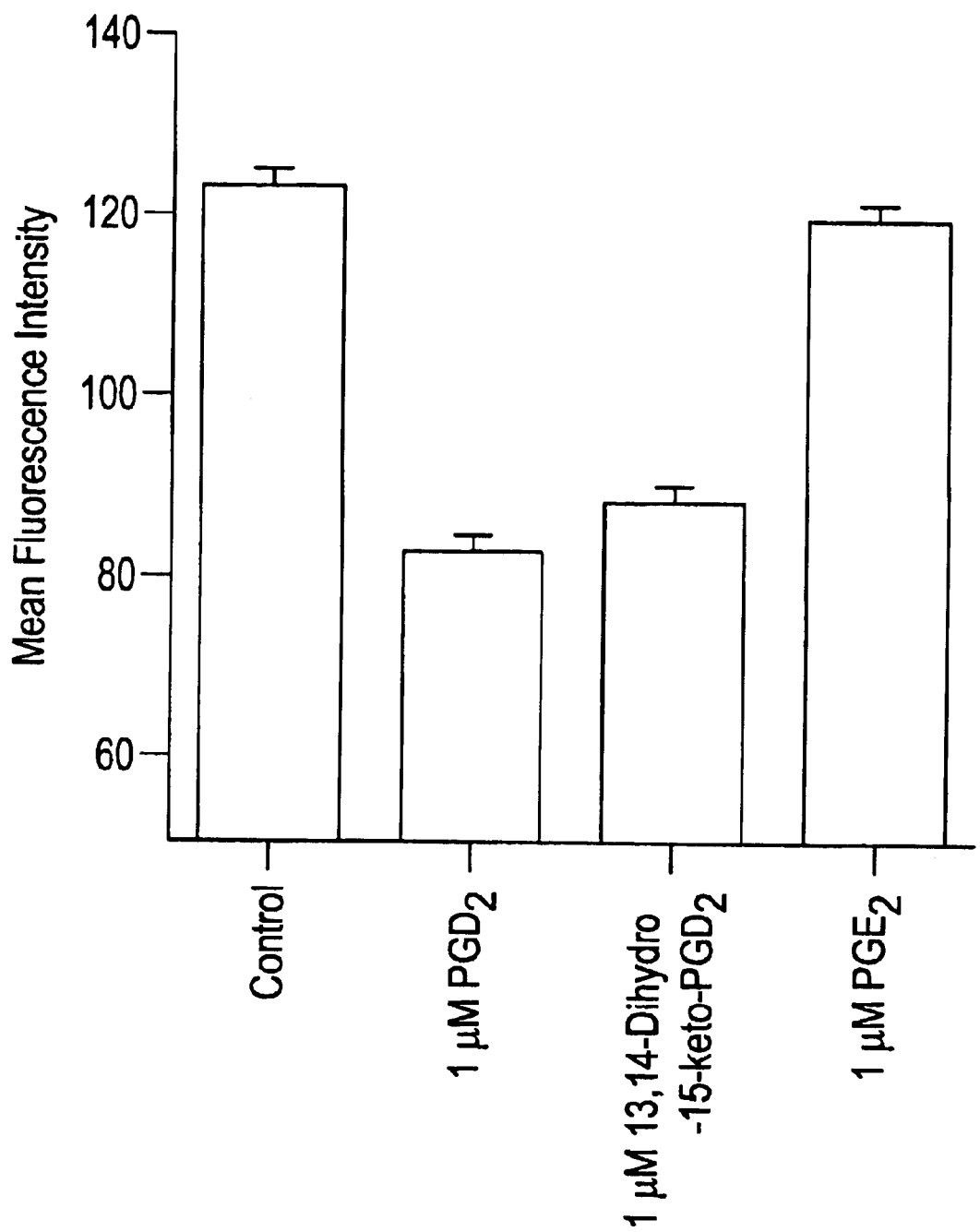
FIG. 4 shows the results of a test, performed in accordance with the method described in Example 6, regarding down modulation from a cell surface, induced by the selective agonist of human CRTH2.

As shown in FIG. 4, $PGD_2$ and 13,14-dihydro-15-keto $PGD_2$, which are selective agonists, induce down modulation of CRTH2 significantly as compared with the control. In contrast, $PGE_2$ exhibiting no agonistic activity, does not exert such an effect. The results show that this method can be used to identify a selective agonist with respect to CRTH2.

INDUSTRIAL APPLICABILITY

As described above, the present invention provides a method for identifying a substance (for example, a selective modulator such as an agonist or antagonist) which acts on a newly found second human $PGD_2$ receptor subtype that differs from the DP receptor, and is useful for treating or preventing various diseases.

What is claimed is:

1. A method for identifying a test substance which modulates human G-protein coupling receptor-like protein (CRTH2) activity, said method comprising:
   (a) contacting human CRTH2 with prostaglandin D2 ($PGD_2$) in the presence of a test substance, and
   (b) comparing activity of the human CRTH2 of (a) with activity of a human CRTH2 contacted with $PGD_2$ in the absence of the test substance, wherein when a change in activity is detected between the human CRTH2 contacted with $PGD_2$ in the presence of the test substance and the human CRTH2 receptor contacted with $PGD_2$ in the absence of the test substance, said test substance is determined to be a modulator of CRTH2 activity.

2. The method according to claim 1, further comprising assaying activity modulating effects of said test substance on DP receptor activity, wherein said assaying is performed by:
   (a) contacting DP receptor with prostaglandin D2 ($PGD_2$) in the presence of the test substance identified in claim 5, and
   (b) comparing activity of the DP receptor of (a) with activity of a DP receptor contacted with $PGD_2$ in the absence of the test substance, wherein when a change in activity is detected between the DP receptor contacted with $PGD_2$ in the presence of the test substance and the DP receptor contacted with $PGD_2$ in the absence of the test substance, said test substance is determined to possess activity modulating effects on DP receptor.

3. The method according to claim 1, wherein said change in activity is a decrease in human CRTH2 activity.

4. The method according to claim 1, wherein said change in activity is an increase in human CRTH2 activity.

5. The method according to claim 1, wherein the change in activity of human CRTH2 is caused by binding of the test substance to human CRTH2.

6. The method according to claim 1, wherein the human CRTH2 is human CRTH2 present on a cell.

7. The method according to claim 6, wherein the change in human CRTH2 activity is an increase in an intracellular concentration of $Ca^{2+}$, or down modulation of CRTH2 at a cell surface.

8. The method according to claim 6, wherein the cell is an established mammalian cell line.

9. The method according to claim 8, wherein the mammalian cell line is a cell line selected from the group consisting of K562 line, Jurkat line, HEK293 line, and CHO line.

10. The method according to claim 1, wherein said $PGD_2$ is labeled with a marker.

11. The method according to claim 1, wherein the test substance is a substance selected from the group consisting of a sedative, a hypnotic, an analgesic, a blood pressure regulating drug, a platelet aggregation inhibitor, a drug for circulatory organs, a drug for suppressing motions of the stomach and the intestine, an anti-gastric ulcer drug, an allergy therapeutic drug, an anti-inflammatory drug, and a drug for preventing and/or treating glaucoma.

* * * * *